United States Patent

Sohda et al.

[11] Patent Number: 5,183,823
[45] Date of Patent: Feb. 2, 1993

[54] PYRIDINE N-OXIDE COMPOUNDS WHICH ARE USEFUL AS HYPOGLYCEMIC AND HYPOLIPIDEMIC AGENTS

[75] Inventors: Takashi Sohda, Takatsuki; Hitoshi Ikeda, Higashiosaka, both of Japan

[73] Assignee: Takeda Chemical Industries, Ltd., Osaka, Japan

[21] Appl. No.: 861,280

[22] Filed: Mar. 31, 1992

[30] Foreign Application Priority Data

Apr. 11, 1991 [JP] Japan .................. 3-078835

[51] Int. Cl.$^5$ .................. C07D 417/12; A61K 31/44
[52] U.S. Cl. .................. 514/358; 514/884; 546/347
[58] Field of Search .................. 546/347; 514/358, 884

[56] References Cited

U.S. PATENT DOCUMENTS

| | | | |
|---|---|---|---|
| 4,002,750 | 1/1977 | Ambrogi et al. | 514/884 |
| 4,444,779 | 4/1984 | Kawamatsu et al. | 424/263 |
| 4,687,777 | 8/1987 | Meguro et al. | 514/342 |

FOREIGN PATENT DOCUMENTS 0050882  8/1987  Japan .................. 546/277

Primary Examiner—C. Warren Ivy
Assistant Examiner—Zinna N. Davis
Attorney, Agent, or Firm—Wenderoth, Lind & Ponack

[57] ABSTRACT

There is disclosed a novel thiazolidinedione derivative of the general formula (I):

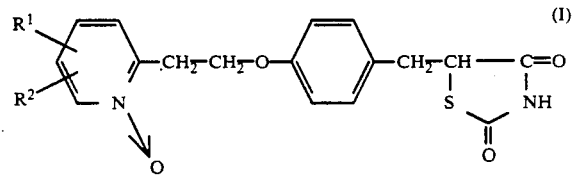

wherein $R^1$ and $R^2$ are the same or different and are a hydrogen atom or a lower alkyl group, or a salt thereof. The thiazolidinedione derivative has hypoglycemic activity and hypolipidemic activity.

10 Claims, No Drawings

PYRIDINE N-OXIDE COMPOUNDS WHICH ARE USEFUL AS HYPOGLYCEMIC AND HYPOLIPIDEMIC AGENTS

FIELD OF THE INVENTION

The present invention relates to novel thiazolidinedione derivatives having hypoglycemic activity and hypolipidemic activity, their production and an antidiabetic agent containing such derivatives.

BACKGROUND OF THE INVENTION

Various biguanide compounds and sulfonylurea compounds have been used as therapeutic agents for diabetes. However, at present, biguanide compounds are scarcely used because they cause lactic acidosis. Although sulfonylurea compounds have strong hypoglycemic activity, they often cause serious hypoglycemia and they must be used with caution.

OBJECTS OF THE INVENTION

The present inventors have intensively studied to find out compounds having hypoglycemic activity without the above drawbacks. As a result, novel thiazolidinedione derivatives having excellent hypoglycemic activity and hypolipidemic activity have been found. Thus, the present invention have been completed.

The main object of the present invention is to provide novel compounds having no drawbacks as described above.

This object as well as other objects and advantages of the present invention will become apparent to those skilled in the art from the following description.

SUMMARY OF THE INVENTION

According to the present invention, there is provided a thiazolidinedione derivative of the general formula (I):

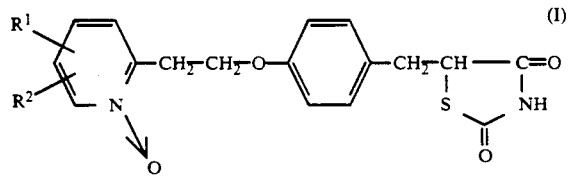

wherein $R^1$ and $R^2$ are the same or different and are a hydrogen atom or a lower alkyl group, or a salt thereof.

The present invention also provides a process for producing the thiazolidinedione derivative of the general formula (I), or a salt thereof which comprises hydrolyzing a compound of the general formula (III):

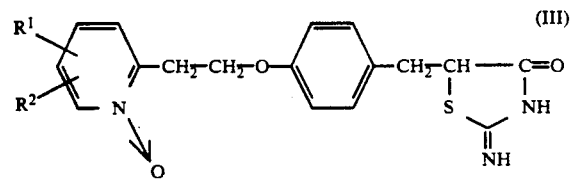

wherein each symbol is as defined above. The compound of the general formula (III) is prepared by reacting a compound of the general formula (II):

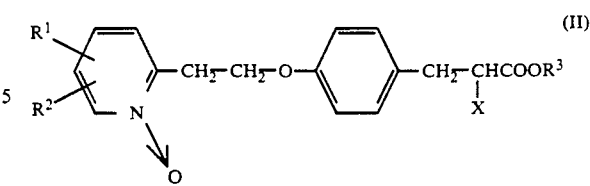

wherein $R^1$ and $R^2$ are as defined above; $R^3$ is a hydrogen atom or a lower alkyl group; and X is a leaving group, with thiourea. Further, the present invention provides an a pharmaceutical composition for treating diabetes comprising as an effective component the thiazolidinedione derivative of the general formula (I) or a pharmacologically acceptable salt thereof.

DETAILED DESCRIPTION OF THE INVENTION

Examples of the lower alkyl group represented by $R^1$ or $R^2$ in the general formulas (I), (II) and (III) include groups having 1 to 4 carbon atoms such as methyl, ethyl, propyl, isopropyl, butyl and the like. Among these groups, groups having 1 to 3 carbon atoms are preferred. The pyridine ring may be substituted with $R^1$ and $R^2$ groups at any positions thereof.

Examples of the lower alkyl group represented by $R^3$ in the general formula (II) include the same lower alkyl groups as those exemplified with respect to the above $R^1$ and $R^2$. Examples of the leaving group represented by X in the general formula (II) include halogen atoms such as chlorine, bromine and iodine, and the like.

The thiazolidinedione derivative of the general formula (I) has an acidic nitrogen atom in the thiazolidine ring. Therefore, the thiazolidinedione derivatives of the general formula (I) (hereinafter referred to as the compound (I)) can exist as its basic salt. Examples of the basic salt of the compound (I) include pharmacologically acceptable salts such as sodium salt, potassium salt, aluminium salt, magnesium salt, calcium salt and the like.

Examples of the compound (I) include the pyridine ring N-oxides of the following compounds:

5-[4-[2-(5-ethyl-2-pyridyl)ethoxy]benzyl]-2,4-thiazolidinedione;

5-[4-[2-(5-methyl-2-pyridyl)ethoxy]benzyl]-2,4-thiazolidinedione;

5-[4-[2-(3-methyl-2-pyridyl)ethoxy]benzyl]-2,4-thiazolidinedione;

5-[4-[2-(6-methyl-2-pyridyl)ethoxy]benzyl]-2,4-thiazolidinedione;

5-[4-[2-(4,6-dimethyl-2-pyridyl)ethoxy]benzyl]-2,4-thiazolidinedione;

5-[4-[2-(4-methyl-2-pyridyl)ethoxy]benzyl]-2,4-thiazolidinedione; and

5-[4-[2-(2-pyridyl)ethoxy]benzyl]-2,4-thiazolidinedione.

The compound (I) and its pharmacologically acceptable salt of the present invention have hypoglycemic activity and hypolipidemic activity. Further, the compound (I) has low toxicity. For example, when the compound obtained in Example 1 hereinafter was orally administered to mice in a dose of 300 mg/kg, no lethal case was observed. Accordingly, the compound (I) or a pharmacologically acceptable salt thereof can be used as a pharmaceutical composition for treating diabetes of mammal including man as they are or by combining with a per se known pharmacologically acceptable carrier, excipient, filler or the like.

Normally, the compound (I) or its pharmacologically acceptable salt can be administered orally in the form of, for example, capsules including soft capsules and micro capsules, powders, granules or the like. If necessary, it can also be administered parenterally in the form of injectable solutions, suppositories, pellets or the like. In the case of oral administration, preferably, it is administered one to three times a day in a daily dose of 0.05 to 10 mg/kg.

The compound (I) of the present invention can be produced by hydrolyzing the compound (III). The compound (III) can be produced by reacting the compound (II) with thiourea.

The reaction of the compound (II) with thiourea is normally carried out in a solvent such as alcohols (e.g., methanol, ethanol, propanol, 2-propanol, butanol, isobutanol, 2-methoxyethanol and the like), dimethyl sulfoxide, sulfolane or the like. The reaction temperature is normally 20° to 180° C., preferably 50° to 150° C. The amount of thiourea to be used is 1 to 2 mol per 1 mol of the compound (II). In this reaction, hydrogen bromide is generated as a by-product as the reaction proceeds. Then, the reaction can be carried out in the presence of a deacidification agent such as sodium acetate, potassium acetate or the like to trap the hydrogen bromide. The deacidification agent is normally used 1 to 1.5 mol per 1 mol of the compound (II).

The compound (III) thus produced can optionally be isolated from a reaction mixture. However, it can be used without isolation in the next acid hydrolysis step.

Hydrolysis of the compound (III) is normally carried out in a suitable solvent in the presence of water and a mineral acid. Examples of the solvent include the solvents used in the reaction between the compound (II) above and thiourea. Examples of the mineral acid include hydrochloric acid, hydrobromic acid, sulfuric acid and the like. The amount of the mineral acid to be used is 0.1 to 20 mol, preferably 0.2 to 10 mol per 1 mol of the compound (III). Water is normally added in large excess. This reaction is normally carried out with warming or heating. The reaction temperature is normally 60° to 150° C. The heating time is normally several hours to twenty and several hours.

The compound (I) or a salt thereof can be isolated and purified by known separation and purification techniques such as concentration, concentration under reduced pressure, crystallization, recrystallization, dissolution in a different solvent, chromatography and the like.

The starting compound (II) can be produced according to the procedure described in JP-A 60-208980.

The following Experiment shows that the compound (I) of the present invention has excellent hypoglycemic activity and hypolipidemic activity.

EXPERIMENT

Hypoglycemic activity and hypolipidemic activity in mice

Test compounds were mixed with laboratory chow diet (CE-2, Clea Japan Inc., Tokyo) in the proportion of 0.005% by weight. The dietary admixture was given freely to KKA$^y$-mice (male, 9 to 10 weeks old) for 4 days. During this period, water was given freely. Blood samples were collected from the orbital venous plexus. Blood sugar level was determined according to glucose oxidase method. Serum tirglyceride level was enzymatically determined by using Kit Cleantech TG-S (Iatron, Tokyo). The results are shown in

TABLE 1

| Compound (Example No.) | Values represent % reduction from control groups. | |
|---|---|---|
| | Hypoglycemic activity (%) | Hypolipidemic activity (%) |
| 1 | 56 | 43 |

As is clear from Table 1, the compound (I) of the present invention has excellent hypoglycemic activity and hypolipidemic activity. Therefore, it is useful as a medicament for treating, for example, diabetes, hyperlipemia and the like.

The compound (I) of the present invention causes neither lactic acidosis nor serious hypoglycemia.

As described hereinabove, according to the present invention, there is provided the novel thiazolidinedione derivatives having excellent hypoglycemic activity and hypolipidemic activity without causing lactic acidosis and hypoglycemia. Therefore, the thiazolidinedione derivatives are useful as a therapeutic agent for treating diabetes and hyperlipemia.

The following examples illustrates the production of the compound (I) of the present invention in detail but are not to be construed to limit the scope thereof.

EXAMPLE 1

A mixture of methyl 2-bromo-3-[4-[2-(5-ethyl-2pyridyl)ethoxy]phenyl]propionate N-oxide (20.0 g), thiourea (3.7 g), sodium acetate (4.0 g) and ethanol (200 ml) was heated under reflux for 3 hours. To the reaction mixture was added 2N hydrochloric acid (200 ml). The mixture was further heated under reflux for 3 hours and concentrated under reduced pressure. The residue was poured into water and the resulting mixture was extracted with chloroform. The chloroform layer was washed with water, dried over anhydrous magnesium sulfate and concentrated under reduced pressure. The oily residue thus obtained was subjected to column chromatography on silica gel. The pyridine ring N-oxide of 5-[4-[2-(5-ethyl-2-pyridyl)ethoxy]benzyl]-2,4-thiazolidinedione (11.0 g, yield: 60%) was obtained from the fraction eluted with chloroform-methanol (50:1, v/v). The N-oxide was recrystallized from ethanol to obtain colorless prisms, m.p. 164°–165° C.

Elemental Analysis for $C_{19}H_{20}N_2O_4S$: Calcd.: C, 61.27; H, 5.41; N, 7.52; Found : C, 61.02; H, 5.33; N, 7.42.

EXAMPLE 2

According to the same manner as that described in Example 1, the pyridine ring N-oxide of 5-[4-[2-(2-pyridyl)ethoxy]benzyl]-2,4-thiazolidinedione was obtained. The N-oxide was recrystallized from chloroform-methanol to obtain colorless prisms, m.p. 187°–188° C.

Elemental Analysis for $C_{17}H_{16}N_2O_4S$: Calcd.: C, 59.29; H, 4.68; H, 8.13; Found : C, 59.44; H, 4.74; H, 7.97.

Example 3

A mixture of methyl 2-bromo-3-[4-[2-(6-methyl-2-pyridyl)ethoxy]phenyl]propionate N-oxide (5.0 g), thiourea (967 mg), sodium acetate (1.04 g) and ethanol (6 ml) was stirred under reflux for 3 hours. The reaction mixture was concentrated under reduced pressure. The residue was neutralized with aqueous saturated sodium bicarbonate. After addition of ether (50 ml), the mixture was stirred. Crystals precipitated were filtered off to obtain the pyridine ring N-oxide of 2-imino-5-[4-[2-(6-methyl-2-pyridiyl)ethoxy]benzyl]-4-thiazolidinone. The N-oxide was recrystallized from chloroform-methanol to obtain colorless needles, m.p. 226°–227° C. (decomp).

Elemental Analysis for $C_{18}H_{19}N_3O_3S$, Calcd.: C, 60.49; H, 5.36; H, 11.76; Found : C, 60.47; H, 5.35; H, 11.72.

Example 4

According to the same manner as that described in Example 3, the pyridine ring N-oxide of 2-imino-5-[4-[2-(3-methyl-2-pyridyl)ethoxy]benzyl]-4-thiazolidinone was obtained. The N-oxide was recrystallized from chloroformmethanol to obtain colorless needles, m.p. 209°–210° C.

Elemental Analysis for $C_{18}H_{19}N_3O_3S$: Calcd.: C, 60.49; H, 5.36; H, 11.76; Found : C, 60.36; H, 5.37; H, 11.60.

Example 5

According to the same manner as that described in Example 3, the pyridine ring N-oxide of 5-[4-[2-(4,6-dimethyl-2-pyridyl)ethoxy]benzyl]-2-imino-4-thiazolidinone was obtained. The N-oxide was recrystallized from methanol to obtain colorless needles, m.p. 187°–188° C.

Elemental Analysis for $C_{19}H_{21}N_3O_3S$: Calcd.: C, 61.44; H, 5.70; H, 11.31; Found : C, 61.48; H, 5.73; H, 11.38.

Example 6

A mixture of the pyridine ring N-oxide of 2-imino5-[4-[2-(6-methyl-2-pyridyl)ethoxy]benzyl]-4-thiazolidinone (3.0 g), 2N hydrochloric acid (30 ml) and ethanol (30 ml) was stirred under reflux for 10 hours. The reaction mixture was concentrated under reduced pressure. The residue was poured into water and extracted with chloroform. The chloroform layer was washed with water and dried over magnesium sulfate and the solvent was distilled off to obtain the pyridine ring N-oxide of 5-[4-[2-(6-methyl-2-pyridyl)ethoxy]benzyl]-2,4-thiazolidinedione (2.8 g, 93%). The N-oxide was recrystallized from chloroform-methanol to obtain colorless plates, m.p. 209°–210° C.

Elemental Analysis for $C_{18}H_{18}N_2O_4S$: Calcd.: C, 60.32; H, 5.06; H, 7.82; Found : C, 59.95; H, 5.09; H, 7.76.

Example 7

According to the same manner as that described in Example 6, the pyridine ring N-oxide of 5-[4-[2-(3-methyl-2-pyridyl)ethoxy]benzyl]-2,4-thiazolidinedione was obtained. The N-oxide was recrystallized from chloroform-methanol to obtain colorless prisms. m.p. 250°–251° C.

Elemental Analysis for $C_{18}H_{18}N_2O_4S$: Calcd.: C, 60.32; H, 5.06; H, 7.82; Found : C, 60.40; H, 5.16; H, 7.77.

Example 8

According to the same manner as that described in Example 6, the pyridine ring N-oxide of 5-[4-[2-(4,6-dimethyl-2-pyridyl)ethoxy]benzyl]-2,4-thiazolidinedione was obtained. The N-oxide was recrystallized from methanol to obtain colorless prisms, m.p. 134°–135° C.

Elemental Analysis for $C_{19}H_{20}N_2O_4.1/4H_2O$: Calcd.: C, 60.54; H, 5.48; H, 7.43; Found : C, 60.29; H, 5.61; H, 7.43.

Example 9

Preparation of tablets

Tablets were prepared according to the following formulation.

| | |
|---|---|
| (1) The compound of Example 1 | 100 g |
| (2) Lactose | 50 g |
| (3) Corn starch | 15 g |
| (4) Calcium carboxymethylcellulose | 44 g |
| (5) Magnesium stearate | 1 g |
| 1000 tablets | 210 g |

All of the ingredients (1), (2) and (3), and 30 g of the ingredient (4) were kneaded with water. The mixture was dried under vacuum and then granulated. The granules thus obtained were mixed with 14 g of the ingredient (4) and 1 g of the ingredient (5). The resulting mixture was compressed into tablets by a tablet machine to produce 1000 tablets of 8 mm diameter containing 100 mg of the ingredient (1) per tablet.

What is claimed is:

1. A thiazolidinedione derivative of the formula (I):

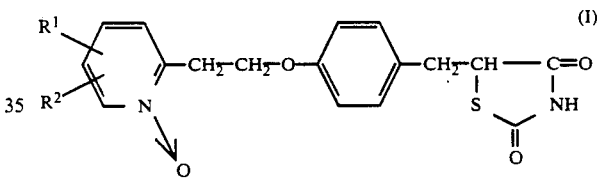

wherein $R^1$ and $R^2$ are the same or different and are a hydrogen atom or a lower alkyl group, or a pharmacologically acceptable salt thereof.

2. A thiazolidinedione derivative according to claim 1 which is pyridine ring N-oxide of 5-[4-[2-(5-ethyl-2-pyridyl)ethoxy]benzyl]-2,4-thiazolidinedione or pharmacologically acceptable salt thereof.

3. A thiazolidinedione derivative according to claim 1 which is pyridine ring N-oxide of 5-[4-[2-(5-methyl2-pyridyl)ethoxy]benzyl]-2,4-thiazolidinedione or pharmacologically acceptable salt thereof.

4. A thiazolidinedione derivative according to claim 1 which is pyridine ring N-oxide of 5-[4-[2-(3-methyl2-pyridyl)ethoxy]benzyl]-2,4-thiazolidinedione or pharmacologically acceptable salt thereof.

5. A thiazolidinedione derivative according to claim 1 which is pyridine ring N-oxide of 5-[4-[2-(6-methyl2-pyridyl)ethoxy]benzyl]-2,4-thiazolidinedione or pharmacologically acceptable salt thereof.

6. A thiazolidinedione derivative according to claim 1 which is pyridine ring N-oxide of 5-[4-[2-(4,6-dimethyl-2-pyridyl)ethoxy]benzyl]-2,4-thiazolidinedione or pharmacologically acceptable salt thereof.

7. A thiazolidinedione derivative according to claim 1 which is pyridine ring N-oxide of 5-[4-[2-(4-methyl-2-pyridyl)ethoxy]benzyl]-2,4-thiazolidinedione or pharmacologically acceptable salt thereof.

8. A thiazolidinedione derivative according to claim 1 which is pyridine ring N-oxide of 5-[4-[2-(2-pyridyl)e- thoxy]benzyl]-2,4-thiazolidineodione or pharmacologically acceptable salt thereof.

9. A pharmaceutical composition for treating diabetes comprising a thiazolidinedione derivative of the formula (I):

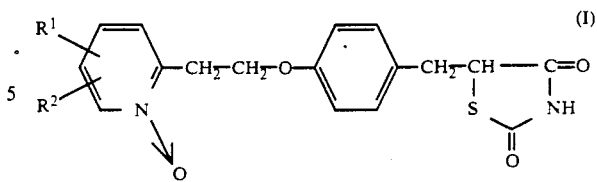

wherein $R^1$ and $R^2$ are the same or different and are a hydrogen atom or a lower alkyl group, or a pharmacologically acceptable salt thereof and a pharmacologically acceptable carrier or diluent.

10. A method for treating diabetes which comprising administering an effective amount of the thiazolidinedione derivative according to claim 1 or a pharmacologically acceptable salt thereof optionally together with a pharmacologically acceptable carrier, excipient or diluent to a patient requiring such a treatment.

* * * * *